United States Patent
Utley et al.

(10) Patent No.: US 7,293,563 B2
(45) Date of Patent: Nov. 13, 2007

(54) SYSTEMS AND METHODS FOR APPLYING A SELECTED TREATMENT AGENT INTO CONTACT WITH TISSUE TO TREAT DISORDERS OF THE GASTROINTESTINAL TRACT

(75) Inventors: David Utley, San Carlos, CA (US); John W Gaiser, Mountain View, CA (US); Rachel Croft, San Francisco, CA (US)

(73) Assignee: Curon Medical, Inc., Fremont, CA (US)

( * ) Notice: Subject to any disclaimer, the term of this patent is extended or adjusted under 35 U.S.C. 154(b) by 301 days.

(21) Appl. No.: 10/912,268

(22) Filed: Aug. 5, 2004

(65) Prior Publication Data

US 2005/0010171 A1   Jan. 13, 2005

Related U.S. Application Data

(60) Division of application No. 09/994,375, filed on Nov. 26, 2001, now Pat. No. 6,790,207, which is a continuation-in-part of application No. 09/304,737, filed on May 4, 1999, now Pat. No. 6,464,697, and a continuation-in-part of application No. 09/090,794, filed on Jun. 4, 1998, now abandoned.

(51) Int. Cl.
    *A61B 19/00*   (2006.01)
(52) U.S. Cl. .................. 128/898; 606/41; 607/133
(58) Field of Classification Search .............. 606/41, 606/42, 45, 46, 48–50; 607/100–102, 116, 607/133; 128/898; 604/20–22
    See application file for complete search history.

(56) References Cited

U.S. PATENT DOCUMENTS

| 1,798,902 A | 3/1931 | Raney |
| 3,517,128 A | 6/1970 | Hines |
| 3,901,241 A | 8/1975 | Allen, Jr. |
| 4,011,872 A | 3/1977 | Komiya |

(Continued)

FOREIGN PATENT DOCUMENTS

DE   43 03 882   2/1995

(Continued)

OTHER PUBLICATIONS

Dallemagne, B., et al.; "Laparoscopic Nissen Fundoplication: Preliminary," Surgical Laparoscopy & Endoscopy. 1991 1(3): 138-43.

(Continued)

*Primary Examiner*—Michael Peffley
(74) *Attorney, Agent, or Firm*—Ryan Kromholz & Manion, S.C.

(57) ABSTRACT

Systems and methods that treat disorders of the gastrointestinal tract by applying one or more treatment agents to tissue at or near the region where abnormal neurological symptoms or abnormal tissue conditions exist. The treatment agent is selected to either disrupt the abnormal nerve pathways and/or to alleviate the abnormal tissue conditions. The treatment agent can include at least one cytokine and/or at least one vanilloid compound to evoke a desired tissue response. The systems and methods can be used a primary treatment modality, or as a neoadjuvent or adjuvant treatment modality.

2 Claims, 3 Drawing Sheets

U.S. PATENT DOCUMENTS

| | | | |
|---|---|---|---|
| 4,196,724 A | 4/1980 | Wirt et al. | |
| 4,313,958 A | 2/1982 | LaHann | |
| 4,411,266 A | 10/1983 | Cosman | |
| 4,423,812 A | 1/1984 | Sato | |
| 4,532,924 A | 8/1985 | Auth et al. | |
| 4,565,200 A | 1/1986 | Cosman | |
| 4,705,041 A | 11/1987 | Kim | |
| 4,901,737 A | 2/1990 | Toone | |
| 4,906,203 A | 3/1990 | Margrave et al. | |
| 4,907,589 A | 3/1990 | Cosman | |
| 4,939,149 A | 7/1990 | Blumberg | |
| 4,943,290 A | 7/1990 | Rexroth et al. | |
| 4,947,842 A | 8/1990 | Marchosky et al. | |
| 4,955,377 A | 9/1990 | Lennox et al. | |
| 4,966,597 A | 10/1990 | Cosman | |
| 4,976,711 A | 12/1990 | Parins et al. | |
| 5,019,075 A | 5/1991 | Spears et al. | |
| 5,021,450 A | 6/1991 | Blumberg | |
| 5,035,696 A | 7/1991 | Rydell | |
| 5,046,512 A | 9/1991 | Murchie | |
| 5,047,028 A | 9/1991 | Qian | |
| 5,057,107 A | 10/1991 | Parins et al. | |
| 5,078,717 A | 1/1992 | Parins et al. | |
| 5,083,565 A | 1/1992 | Parins | |
| 5,084,044 A | 1/1992 | Quint | |
| 5,088,979 A | 2/1992 | Filipi et al. | |
| 5,094,233 A | 3/1992 | Brennan | |
| 5,100,423 A | 3/1992 | Fearnot | |
| 5,106,360 A | 4/1992 | Ishiwara et al. | |
| 5,122,137 A | 6/1992 | Lennox | |
| 5,125,928 A | 6/1992 | Parins et al. | |
| 5,156,151 A | 10/1992 | Imran | |
| 5,190,541 A | 3/1993 | Abele et al. | |
| 5,197,963 A | 3/1993 | Parins | |
| 5,197,964 A | 3/1993 | Parins | |
| 5,205,287 A | 4/1993 | Erbel et al. | |
| 5,215,103 A | 6/1993 | Desai | |
| 5,232,444 A | 8/1993 | Just et al. | |
| 5,236,413 A | 8/1993 | Fiering | |
| 5,242,441 A | 9/1993 | Avitall | |
| 5,254,126 A | 10/1993 | Filipi et al. | |
| 5,256,138 A | 10/1993 | Vurek et al. | |
| 5,257,451 A | 11/1993 | Edwards et al. | |
| 5,263,493 A | 11/1993 | Avitall | |
| 5,275,162 A | 1/1994 | Edwards et al. | |
| 5,275,608 A | 1/1994 | Forman et al. | |
| 5,275,610 A | 1/1994 | Eberbach | |
| 5,277,201 A | 1/1994 | Stern | |
| 5,281,216 A | 1/1994 | Klicek | |
| 5,281,217 A | 1/1994 | Edwards et al. | |
| 5,281,218 A | 1/1994 | Imran | |
| 5,290,286 A | 3/1994 | Parins | |
| 5,292,321 A | 3/1994 | Lee | |
| 5,293,869 A | 3/1994 | Edwards et al. | |
| 5,309,910 A | 5/1994 | Edwards et al. | |
| 5,313,943 A | 5/1994 | Houser et al. | |
| 5,314,466 A | 5/1994 | Stern et al. | |
| 5,316,020 A | 5/1994 | Truffer | |
| 5,324,284 A | 6/1994 | Imran | |
| 5,328,467 A | 7/1994 | Edwards et al. | |
| 5,334,196 A | 8/1994 | Scott et al. | |
| 5,336,222 A | 8/1994 | Durgin, Jr. et al. | |
| 5,345,936 A | 9/1994 | Pomeranz et al. | |
| 5,348,554 A | 9/1994 | Imran et al. | |
| 5,363,861 A | 11/1994 | Edwards et al. | |
| 5,365,926 A | 11/1994 | Desai | |
| 5,365,945 A | 11/1994 | Halstrom | |
| 5,366,490 A | 11/1994 | Edwards et al. | |
| 5,368,557 A | 11/1994 | Nita et al. | |
| 5,368,592 A | 11/1994 | Stern et al. | |
| 5,370,675 A | 12/1994 | Edwards et al. | |
| 5,370,678 A | 12/1994 | Edwards et al. | |
| 5,383,876 A | 1/1995 | Nardella | |
| 5,383,917 A | 1/1995 | Desai et al. | |
| 5,385,544 A | 1/1995 | Edwards et al. | |
| 5,397,339 A | 3/1995 | Desai | |
| 5,398,683 A | 3/1995 | Edwards et al. | |
| 5,401,272 A | 3/1995 | Perkins | |
| 5,403,311 A | 4/1995 | Abele et al. | |
| 5,409,453 A | 4/1995 | Lundquist et al. | |
| 5,409,483 A | 4/1995 | Campbell et al. | |
| 5,415,657 A | 5/1995 | Taymor-Luia | |
| 5,421,819 A | 6/1995 | Edwards et al. | |
| 5,423,808 A | 6/1995 | Edwards et al. | |
| 5,423,811 A | 6/1995 | Ellman et al. | |
| 5,423,812 A | 6/1995 | Ellman et al. | |
| 5,431,914 A | 7/1995 | Adekunle et al. | |
| 5,433,739 A | 7/1995 | Sluijter et al. | |
| 5,435,805 A | 7/1995 | Edwards | |
| 5,441,499 A | 8/1995 | Fritzsch | |
| 5,443,470 A | 8/1995 | Stern et al. | |
| 5,454,782 A | 10/1995 | Perkins | |
| 5,456,662 A | 10/1995 | Edwards et al. | |
| 5,456,682 A | 10/1995 | Edwards et al. | |
| 5,458,596 A | 10/1995 | Lax et al. | |
| 5,458,597 A | 10/1995 | Edwards et al. | |
| 5,465,717 A | 11/1995 | Imran et al. | |
| 5,470,308 A | 11/1995 | Edwards et al. | |
| 5,471,982 A | 12/1995 | Edwards et al. | |
| 5,472,441 A | 12/1995 | Edwards et al. | |
| 5,484,400 A | 1/1996 | Edwards et al. | |
| 5,486,161 A | 1/1996 | Lax et al. | |
| 5,490,984 A | 2/1996 | Freed | |
| 5,496,271 A | 3/1996 | Burton et al. | |
| 5,496,311 A | 3/1996 | Abele et al. | |
| 5,500,012 A | 3/1996 | Brucker et al. | |
| 5,505,728 A | 4/1996 | Ellman et al. | |
| 5,505,730 A | 4/1996 | Edwards | |
| 5,507,743 A | 4/1996 | Edwards et al. | |
| 5,509,419 A | 4/1996 | Edwards et al. | |
| 5,514,130 A | 5/1996 | Baker | |
| 5,514,131 A | 5/1996 | Edwards et al. | |
| 5,520,684 A | 5/1996 | Imran | |
| 5,531,676 A | 7/1996 | Edwards et al. | |
| 5,531,677 A | 7/1996 | Lundquist et al. | |
| 5,536,240 A | 7/1996 | Edwards et al. | |
| 5,536,267 A | 7/1996 | Edwards et al. | |
| 5,540,655 A | 7/1996 | Edwards et al. | |
| 5,549,644 A | 8/1996 | Lundquist et al. | |
| 5,554,110 A | 9/1996 | Edwards et al. | |
| 5,556,377 A | 9/1996 | Rosen et al. | |
| 5,558,672 A | 9/1996 | Edwards et al. | |
| 5,558,673 A | 9/1996 | Edwards et al. | |
| 5,562,720 A | 10/1996 | Stern et al. | |
| 5,571,116 A | 11/1996 | Bolanos et al. | |
| 5,578,007 A | 11/1996 | Imran | |
| 5,588,432 A | 12/1996 | Crowley | |
| 5,588,960 A | 12/1996 | Edwards et al. | |
| 5,599,345 A | 2/1997 | Edwards et al. | |
| 5,599,346 A | 2/1997 | Edwards et al. | |
| 5,609,151 A | 3/1997 | Mulier et al. | |
| 5,624,439 A | 4/1997 | Edwards et al. | |
| 5,672,153 A | 9/1997 | Lax et al. | |
| 5,676,674 A | 10/1997 | Bolanos et al. | |
| 5,686,425 A | 11/1997 | Lee | |
| 5,688,266 A | 11/1997 | Edwards et al. | |
| 5,688,490 A | 11/1997 | Tournier et al. | |
| 5,702,438 A | 12/1997 | Avitall | |
| 5,709,224 A | 1/1998 | Behl et al. | |
| 5,713,891 A | 2/1998 | Poppas | |
| 5,732,698 A | 3/1998 | Swanson et al. | |
| 5,738,096 A | 4/1998 | Ben-Haim | |
| 5,823,197 A | 10/1998 | Edwards | |
| 5,830,213 A | 11/1998 | Panescu et al. | |

| | | | |
|---|---|---|---|
| 5,836,874 A | 11/1998 | Swanson et al. | |
| 5,840,762 A | 11/1998 | Bernstein et al. | |
| 5,860,974 A | 1/1999 | Abele | |
| 5,871,483 A | 2/1999 | Jackson et al. | |
| 5,962,532 A | 10/1999 | Campbell et al. | |
| 6,006,755 A | 12/1999 | Edwards | |
| 6,044,846 A | 4/2000 | Edwards | |
| 6,056,744 A | 5/2000 | Edwards | |
| 6,073,052 A | 6/2000 | Zelickson et al. | |
| 6,077,257 A | 6/2000 | Edwards et al. | |
| 6,156,032 A * | 12/2000 | Lennox | 606/41 |
| 6,180,658 B1 | 1/2001 | Anzalone | |
| 6,201,014 B1 | 3/2001 | Gardiner | |
| 6,238,335 B1 | 5/2001 | Silverman et al. | |
| 6,238,872 B1 | 5/2001 | Mosseri | |
| 6,251,063 B1 | 6/2001 | Silverman et al. | |
| 6,251,064 B1 | 6/2001 | Silverman et al. | |
| 6,358,197 B1 | 3/2002 | Silverman et al. | |
| 6,358,245 B1 | 3/2002 | Edwards et al. | |
| 6,409,723 B1 * | 6/2002 | Edwards | 606/41 |
| 6,425,877 B1 * | 7/2002 | Edwards | 604/21 |
| 6,440,128 B1 | 8/2002 | Edwards et al. | |
| 6,464,689 B1 * | 10/2002 | Qin et al. | 606/1 |
| 6,464,697 B1 | 10/2002 | Edwards et al. | |
| 6,790,207 B2 * | 9/2004 | Utley et al. | 606/41 |
| 6,802,841 B2 * | 10/2004 | Utley et al. | 606/41 |
| 2001/0006982 A1 | 7/2001 | Cruz et al. | |
| 2004/0039052 A1 | 2/2004 | Cruz et al. | |
| 2005/0010162 A1 * | 1/2005 | Utley et al. | 604/20 |

FOREIGN PATENT DOCUMENTS

| | | |
|---|---|---|
| DE | 38 38 840 | 2/1997 |
| EP | 0 139 607 | 5/1985 |
| EP | 0 401 903 | 5/1990 |
| EP | 0 608 609 | 8/1994 |

OTHER PUBLICATIONS

Hinder, R.A., et al.; "The Technique of Laparoscopic Nissen Fundoplication: Surgical Laparoscopy and Endoscopy," 1992.2(3): 265-272.

Karlstrom, L.H. et al.; "Ectopic Jejunal Pacemakers and Enterogastric Reflux Roux Gastrectomy: Effect of Intestinal Pacing," Surgery 1989. 106(3): 486-495.

Kelly, K.,A. et al.; "Duodenal-Gastric Reflux and Slowed Gastric Emptying by Electrical Pacing of the Canine Duodenal Pacesetter Potential," Gastroenterology, 1977, 72(3): 429-33.

Urshel, J.D.; "Complications of Antireflux Surgery," Am. J Surg. 1993. 166(1): 68-70.

Kaneko, et al.; "Physiological Laryngeal Pacemaker" May 1985, Trans Am Soc. Artif Intern Organs, vol. XXXI, pp. 293-296.

Mugica et al.; Neurostimulation: An Overview, Chapter 21, Preliminary Test of a Muscular Diaphragm Pacing System on Human Patients, 1985. pp. 3, 263-279.

Rice et al.; Endoscopic Paranasal Sinus Surgery, Chapter 5, Functional Endocsopic Paranasal Sinus Surgery, The Technique of Messerklinger; Raven Press, 1988, pp. 75-104.

Rice et al.; Endoscopic Parsanasal Sinus Surgery, Chapter 6, Total Endoscopic Sphenoethmoidectomy, The Technique of Wigand; Raven Press, 1988, pp. 105-125.

Mugica et al; "Direct Diaphragm Stimulation," Jan. 1987 PACE, vol. 10, pp. 252-256.

* cited by examiner

SYSTEMS AND METHODS FOR APPLYING A SELECTED TREATMENT AGENT INTO CONTACT WITH TISSUE TO TREAT DISORDERS OF THE GASTROINTESTINAL TRACT

RELATED APPLICATIONS

This application is a divisional of U.S. patent application Ser. No. 09/994,375, filed Nov. 26, 2001, now U.S. Pat. No. 6,790,207, which is a continuation-in-part of U.S. patent application Ser. No. 09/304,737, filed May 4, 1999, now U.S. Pat. No. 6,464,697, and a continuation-in-part of U.S. patent application Ser. No. 09/090,794, filed Jun. 4, 1998 and entitled "Method for Treating a Sphincter" (now abandoned).

FIELD OF THE INVENTION

In a general sense, the invention is directed to systems and methods for treating interior tissue regions of the body. More specifically, the invention is directed to systems and methods for treating dysfunctions of organs and tissue in the gastrointestinal tract.

BACKGROUND OF THE INVENTION

Disorders of organs or tissue of the gastrointestinal tract can be caused by as neurological factors (such as abnormal nerve impulses) or by physical factors (such as excess tissue volume).

For example, intestinal motility (i.e., the contraction of intestinal muscles and the propulsion and movement of the lumenal contents) is controlled by nerves and hormones, as well as by electrical activity in the muscular wall of the intestine. There are several disorders that involve abnormal motility and result in abnormal and uncomfortable visceral sensations. These disorders can cause significant discomfort and distress in the absence of gross physical abnormality of the intestine.

For example, irritable bowel syndrome (IBS) is a common disorder of the intestines. IBS can lead to crampy pain, gassiness, bloating, and changes in bowel habits. Some people with IBS have constipation (difficult or infrequent bowel movements) others have diarrhea (frequent loose stools, often with an urgent need to move the bowels); and some people experience both symptoms intermittently. Sometimes the person with IBS has a crampy urge to move the bowels, but cannot do so. The cause of IBS is not known, and as yet there is no cure. IBS can be characterized as a functional disorder because there is no sign of disease when the intestine is examined, often IBS is just a mild annoyance, but for some people it can be disabling.

Dyspepsia is another example. Dyspepsia is literally translated as 'bad digestion" and is commonly known as indigestion. Motility-like dyspepsia causes persistent or recurring abdominal pain that is centered in the upper abdomen. People with motility associated dyspepsia also may experience bloating, nausea, burping and a feeling of fullness that occurs soon after eating. It is an extremely common symptom complex, affecting as much as one-fourth of the United States adult population.

There are other disorders affecting the gastrointestinal tract that are characterized by abnormal tissue conditions not associated with neural abnormalities.

SUMMARY OF THE INVENTION

The invention provides systems and methods that treat disorders of the gastrointestinal tract by applying one or more treatment agents to tissue at or near the region where abnormal neurological symptoms and/or abnormal tissue conditions exist. The treatment agent is selected to either disrupt abnormal nerve pathways, e.g., associated with dysmotility and/or discomfort, and/or to alleviate abnormal tissue conditions, e.g., to stiffen tissue in order to alleviate disease.

One aspect of the invention provides systems and methods that apply a selected treatment agent into contact with tissue at or in a region of the gastrointestinal tract where dysmotility and/or abnormal visceral sensations exist. The application of the treatment agent can provide relief from the pain and symptoms of nerve-related gastrointestinal disorders, such as irritable bowel syndrome or motility-like dyspepsia. Application of the treatment agent may also attenuate the dysmotility and alleviate the dysfunction itself. The systems and methods may be used as either a primary treatment modality, or may be applied before, during, or after some other primary intervention.

According to this aspect of the invention, the treatment agent includes at least one vanilloid compound. Presence of the vanilloid compound evokes a desired tissue response, which includes at least one of the following, e.g., the interruption of nerve impulses which leads to a reduction of the symptoms that are associated with abnormal nerve impulses, the diminution of pain impulses, the attenuation of the dysmotility, and/or the alleviation the disease state itself. The vanilloid treatment agent may be applied to surface tissue, or, alternatively, it may be injected into subsurface tissue. In one embodiment, the systems and methods can also apply energy to the tissue region td form at least one lesion in conjunction with application of the treatment agent.

Another aspect of the invention provides systems and methods that apply a selected treatment agent into contact with tissue at or in a region where an abnormal tissue condition exists in order to affect normal functionality.

According to this aspect of the invention, the treatment agent includes at least one sub-type of a cytokine. Presence of the cytokine evokes a desired tissue response, which can include, e.g., an initiation of a localized healing process including influx of white blood cells and fibroblasts, followed by deposition of collagen, and subsequent tissue compliance reduction and tightening. These effects will result in a reduction of tissue volume. The cytokine treatment agent may be applied to surface tissue, or, alternatively, it may be injected into subsurface tissue, including the submucosa.

Features and advantages of the inventions are set forth in the following Description and Drawings, as well as in the appended Claims.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION OF THE PREFERRED EMBODIMENTS

This Specification discloses various systems and methods for treating dysfunctions of organs or tissue in the gastrointestinal tract. Still, it should be appreciated that the disclosed systems and methods are applicable for use in treating other dysfunctions elsewhere in the body, e.g., for treating sphincter barrier dysfunctions in the lower gastrointestinal tract or in the upper gastrointestinal tract. The systems and methods that embody features of the invention are adaptable for use with catheter-based systems and surgical techniques, as well as systems and surgical Techniques that are not necessarily catheter-based.

I. System Overview

Figure 1A:
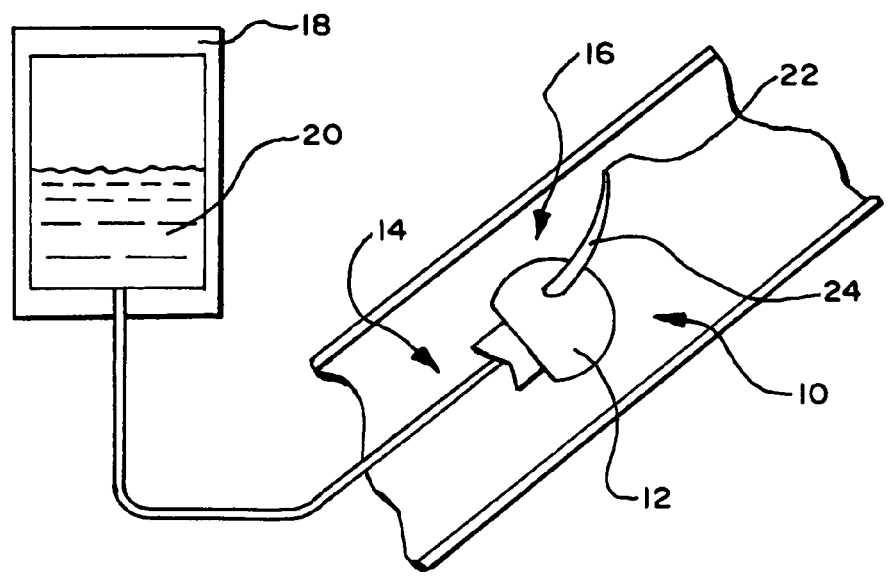
FIGS. 1A and 1B are schematic views of a system for treating tissue that includes a treatment device with a tissue piercing member that embodies features of the invention, FIG. 1A showing the treatment device deployed in a tissue region and FIG. 1B showing the treatment device piercing the tissue region to inject a treatment agent.
Figure 1B:
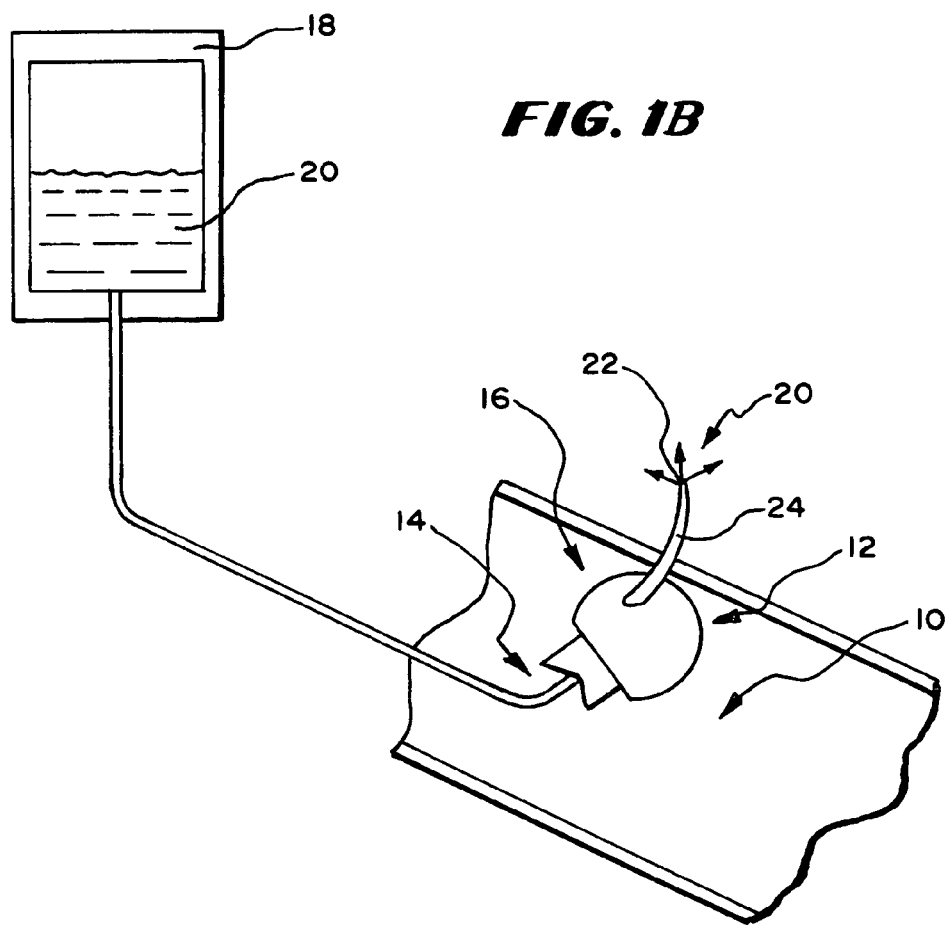

A tissue treatment system 10 that embodies features of the invention is shown in FIGS. 1A and 1B. The tissue treatment system 10 includes a tissue treatment device 12 and an apparatus 14 to deliver the tissue treatment device 12 to a tissue region 16 targeted for treatment. The treatment system 10 also includes a source 18 of a treatment agent 20.

A. The Tissue Treatment Device

The tissue treatment device 12 serves to apply the treatment agent 20 to the targeted tissue region 16 to obtain a desired therapeutic effect. The therapeutic effect can comprise either alteration of nerve impulse pathways in the region 16 or a physical alteration of tissue characteristics in the region 16.

The tissue treatment device 12 includes one or more agent delivery ports 22. The one or more delivery ports 22 can apply the treatment agent 20 to surface tissue in the region 16. Desirably (as FIG. 1A shows), the port 20 is located at the end of a tissue piercing member 24. In this arrangement, the treatment agent 20 may be injected into subsurface tissue.

Figure 2A:
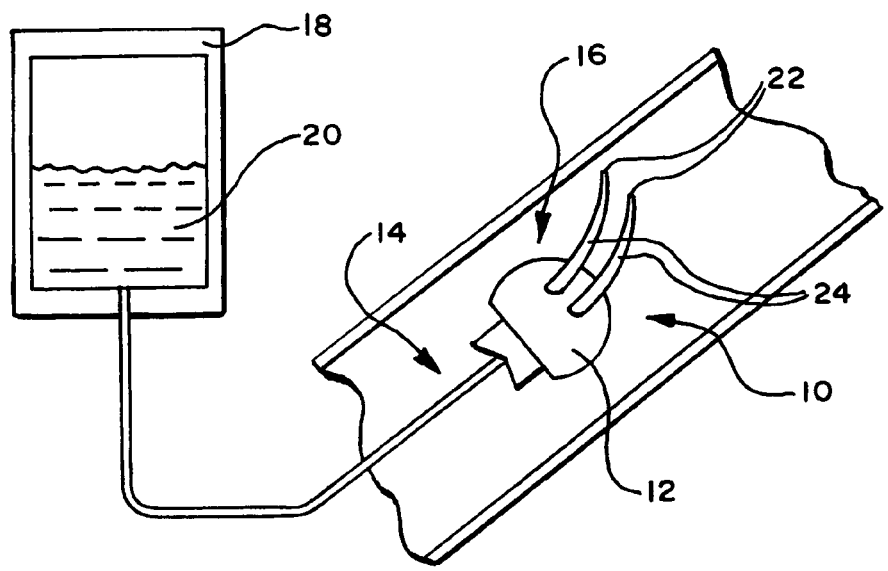
FIGS. 2A and 2B are schematic views of a system for treating tissue that includes a treatment device with multiple tissue piercing members that embodies features of the invention, FIG. 2A showing the treatment device deployed in a tissue region and FIG. 2B showing the treatment device piercing the tissue region to inject a treatment agent.
Figure 2B:
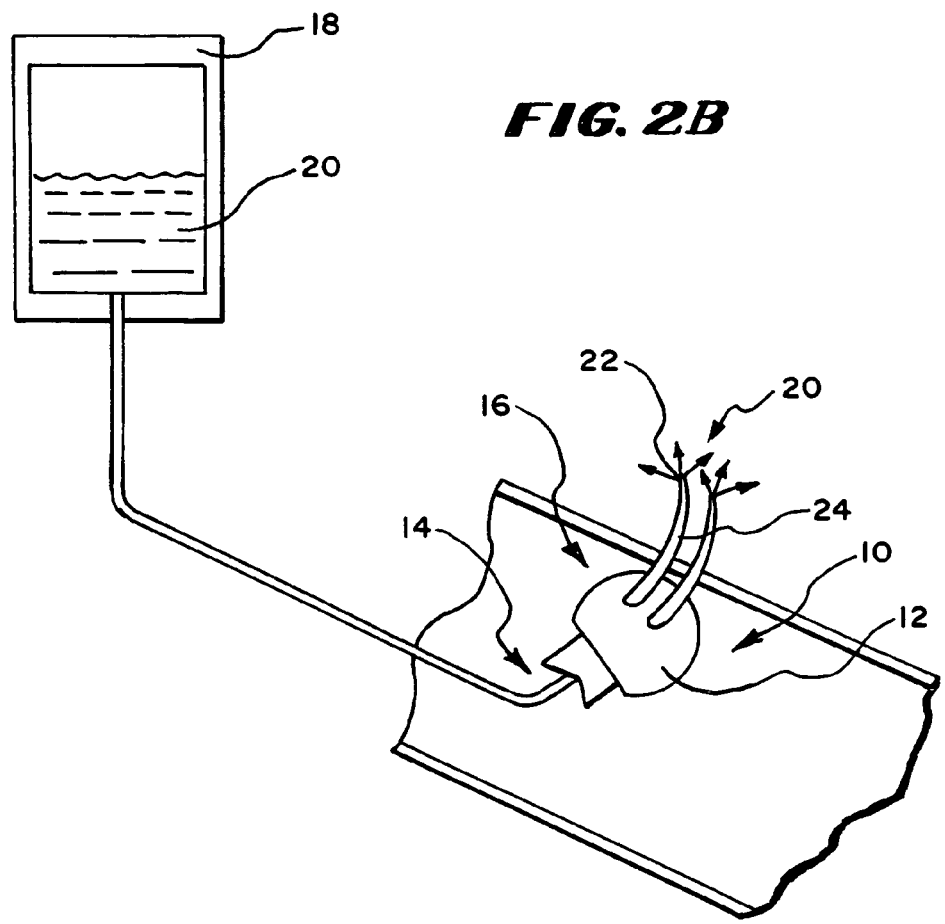

The tissue treatment device 12 can include single or multiple ports 22 located single or multiple tissue piercing members 24 to inject the treatment agent 20. As FIGS. 1A and 1B show, a single tissue piercing member 24 (with a single port 22) may be used. Alternatively, as FIGS. 2A and 2B show, the treatment device 24 can carry multiple tissue piercing members 24, each with a port 22. Desirably, the multiple tissue piercing members 24 are arranged in a spaced-apart array, to apply the treatment agent 20 in a prescribed pattern at the targeted site.

Alternatively, the tissue treatment device 12 may employ air powered, needle-less injection technology.

B. The Delivery Device

The configuration of the delivery apparatus 14 for the device 12 can also vary, depending upon the accessibility of the treatment site and the particular treatment objectives desired.

Figure 3:
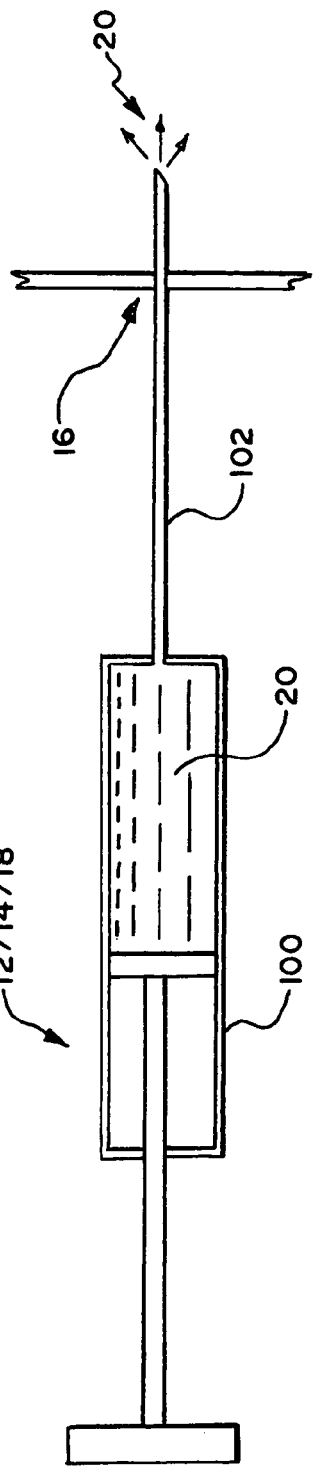
FIG. 3 is an embodiment of a tissue treatment device that takes the form of a syringe and a needle for injecting a treatment agent into a tissue region that can be visualized from outside the body.

If the treatment site can be directly visualized the delivery apparatus 14, the source 18, and the treatment device 12 can comprise a syringe 100 and a needle 102, as FIG. 3 shows.

Figure 4:
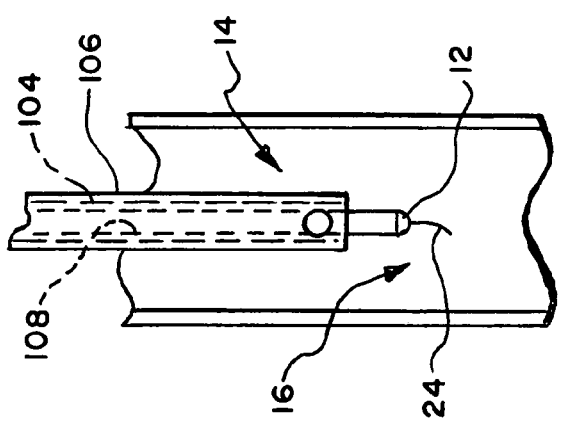
FIG. 4 is an embodiment of a tissue treatment device for injecting a treatment agent into a tissue region that cannot be visualized from outside the body.

If the treatment site can not be directly visualized or is otherwise not as readily accessible, the delivery apparatus 14 can comprise an endoscope 106 having an interior lumen 104 passed down the esophagus through the mouth, as FIG. 4 shows. In this arrangement, the treatment device 12 is desirably carried on the distal end of a catheter tube 108 for passage through the endoscope lumen 104 to the targeted site. A guidewire may be used, if desired, to further facilitate deployment of the endoscope and treatment device to the targeted site.

C. The Tissue Treatment Agent

The treatment agent 20 is selected from a group of candidate agents based upon the physiologic effect or effects that are desired. One or more candidate agents may be applied, either as a primary treatment modality, a neoadjuvent treatment modality, or an adjuvent treatment modality.

In the illustrated embodiment, the group consists essentially of two candidate agents: (1) Vanilloid Compounds, and (2) Cytokine Sub-Types.

1. Vanilloid Compounds

The treatment agent 20 can comprise a vanilloid compound. Vanilloid compounds have a unique capacity to bind to a membrane receptor in sensory neurons. Capsaicin is one of many vanilloid compounds. Capsaicin is a powerful basic compound which is derived from chili peppers.

The specific neuron for capsaicin is deemed "VRl". This receptor is expressed only on small unmyelinated C-fibers (nerves typically involved in special visceral sensation and pain).

Exposure to vanilloid compounds variably reduces the responsiveness of the neuron to stimuli. In many cases, the neuron may actually degenerate either temporarily or permanently, thus impairing transmission of pain signals or other special sensory signals.

The term "vanilloid compound" as used herein means a compound or a mixture of compounds having a biologically active vanillyl group. vanilloid compounds include both naturally occurring vanilloids, synthetic vanilloids, pharmaceutically acceptable salts of the vanilloid compound (whether natural or synthetic) as well as pharmaceutically acceptable derivatives and/or analogues thereof (whether natural or synthetic). Examples of natural vanilloid compounds include both the crude extracts and the purified extracts of active vanilloid compounds from: capsicum, cayenne pepper, black pepper, paprika, cinnamon, clove, mace, mustard, ginger, turmeric, papaya seed and the cactus-like plant Euphorbia resinifera.

Synthetic vanilloid compounds such as synthetic capsaicin are disclosed in WO 96/40079, which is incorporated herein by reference. The vanilloid compound family includes: Capsaicin; Dihydrocapsaicin: Nordihydrocapsaicin; Homocapsaicin: Homodihydrocapsaicin. Alternatively, resiniferotoxin (RTX) is derived from the euphorbia cactus and is considered a capsaicin-like compound. This substance also activates the VRl receptor and attenuates or eliminates afferent nerve function, although it may not illicit the rapid heat sensation that other vanilloids produce.

Other examples of vanilloid compounds include capsaicin ((E)-(N)-[(4-hydroxy-3-methoxyphenyl)-methyl]-8-methyl- 6-nonenamide); eugenol(2-methoxy-4-(2-propenyl)phenol); zingerone(4-(4-hydroxy-3-methoxyphenyl)-2-butanone); curcumin(1,7-bis(4-hydroxy-3-methoxyphenyl)-1,6-heptadiene-3,5-dione); piperine(1-[5-(1,3-benzodioxol-5-yl)-1-oxo-2,4-pentadienyl]piperidine); resiniferatoxin(6,7-deepoxy-6,7-didehydro-5-deoxy-21-dephenyl-21-(phenylmethyl)-20-(4-hydroxy-3effective salts, analogues, derivatives or equivalents thereof.

The treatment agent 20 can include capsaicin, another vanilloid compound, RTX, or combination thereof, alone or in combination with other substances (which will be generically called a vanilloid-containing treatment agent 20).

The vanilloid-containing treatment agent can be applied through the port 22 or ports 22 to the mucosal lining or extrinsically to the outside of an organ. The vanilloid-containing treatment agent can also be injected into the targeted tissue region or organ wall.

The treatment agent 20 can be a solution, a gel, a powder, a pellet, or other form. The treatment agent may be released immediately, or, be a sustained release product such as a slow released implant, slow release gel, coated pellet, microsphere, or other form.

The vanilloid-containing treatment agent 20 may be applied or injected as primary therapy, or, as a neoadjuvant or adjuvant procedure. For example, RF energy may be used to incite a wound, followed by application of the vanilloid-containing treatment agent to facilitate exuberant wound healing.

In dyspepsia and irritable bowel syndrome, the use of a vanilloid-containing treatment agent can serve to diminish the pain impulses or could attenuate the dysmotility and alleviate the disease state.

An example of vanilloid materials that can be used is produced by Afferon and is called RTX, which has been instilled into the lumen of the urinary bladder for the treatment of urge incontinence. There are also several topical, over-the-counter capsaicin products for topical analgesic applications.

2. Cytokine Sub-Types

The treatment agent 20 can include one or more subtypes of cytokines. A cytokine, in the natural state within the body, is a protein produced and released by a biological cell that has an effect on the local environment surrounding the cell. Cytokines are involved in many cellular processes, such as wound healing. The mechanism of action would depend on the specific cytokine utilized.

The term "cytokine subtype" as used herein means any polypeptide that affects the functions of other cells, and is a molecule which modulates interactions between cells in the immune or inflammatory response. A cytokine subtype includes, but is not limited to monokines and lymphokines regardless of which cells produce them. For instance, a monokine is generally referred to as being produced and secreted by a mononuclear cell, such as a macrophage and/or monocyte but many other cells produce monokines, such as natural killer cells, fibroblasts, basophils, neutrophils, endothelial cells, brain astrocytes, bone marrow stromal cells, epideral keratinocytes, and B-lymphocytes. Lymphokines are generally referred to as being produced by lymphocyte cells. Examples of cytokine subtypes include, but are not limited to, interleukin-1. (IL-1), tumor necrosis factor-alpha (TNF alpha) and tumor necrosis factor beta (TNF beta).

Other cytokine subtypes include TGF-β (transforming growth factor β); PDGF (platelet derived growth factor) b-FGF (basic fibroblast growth factor): IGF-l (insulin-like growth factor 1); EGF (epidermal growth factor); and VEGF. Some of these cytokines are available commercially, could be produced commercially, or can be extracted from a persons harvested platelets (platelet releasates). The effects of a given cytokine upon tissue physiology can include one or more of the following: smooth muscle and fibroblast mitogenic effects (induces division and growth of cells); stimulation of the release of cytokines from other cells; chemoattractant (bringing new healing cells into local region); decrease of collagen enzyme activity allowing collagen to build up; inflammation; and angiogenesis (development of new blood vessels).

The treatment agent 20 can include a cytokine sub-type or combination of cytokine sub-types, alone or in combination with other substances. The cytokine-containing treatment agent can be applied by the port or ports 22 to the tissue or organ wall, or injected into the tissue or organ wall.

The cytokine-containing treatment agent 20 can be a solution, a gel, a powder, a pellet, or other form. The treatment agent may be released immediately, or, be a sustained release product such as a slow released implant, slow release gel, coated pellet, microsphere, or other form.

The cytokine-containing agent 20 may be applied or injected as primary therapy, or, as a neoadjuvant or adjuvant procedure. For example, radio frequency (RF) energy may be used to induce the wound healing process, followed by cytokine application to facilitate more exuberant wound healing.

The application of a single cytokine or mixture thereof, as primary, neoadjuvant, or adjuvant therapy for abnormal tissue conditions (e.g., excess tissue volume) could have the various mechanical and therapeutic effects. With or without an inciting wound event (such as RF), cytokines can serve to initiate the process of healing within the local region. This process includes, but is not limited to, influx of white blood cells and macrophages, stimulation of fibroblast and smooth muscle division and collagen secretion, new blood vessel growth, wound contraction and tightening, maturation of the new or existing collagen framework, and reduced tissue compliance. These tissue effects could improve the compliance and reduce the tissue volume.

Examples of cytokine materials that can be used include commercially available Regranex, which is recombinant human PDGF-BB. This material has been applied as a gel for promoting the healing of diabetic foot ulcers. Platelet granules contain many of the cytokines listed above, and the cytokines can be extracted with a fairly simple technique (platelet releasates). Platelets (harvested as a pooled platelet product or from autologous donation) provide a source of cytokines for extraction. TGF-β and PDGF are considered to be the most important substances for the purpose of initiating the wound healing process.

Various features of the invention are set forth in the following claims.

We claim:

1. A method of treating tissue within a body comprising
selecting at least one treatment agent comprising at least one of a vanilloid compound and a cytokine compound,
providing a source of the treatment agent,
deploying an endoscope passed down an esophagus through a mouth to a targeted tissue region, the endoscope having an interior lumen, visualizing the targeted tissue region with the endoscope, deploying through the interior lumen of the endoscope a catheter carrying on its distal end a tissue-piercing element adjacent to the targeted tissue region visualized by the endoscope, coupling the catheter to the source of the treatment agent, and applying through the tissue-piercing element the treatment agent into contact with the targeted tissue region visualized by the endoscope.

2. A method according to claim 1 wherein the applying includes injecting the treatment agent into subsurface tissue in the targeted tissue region.

* * * * *